United States Patent [19]

Schulte-Huermann et al.

[11] 4,268,458

[45] May 19, 1981

[54] PROCESS FOR THE PREPARATION OF N-ALKYLATED AROMATIC AMINES

[75] Inventors: Werner Schulte-Huermann; Heinz P. Hemmerich, both of Krefeld, Fed. Rep. of Germany

[73] Assignee: Bayer Aktiengesellschaft, Leverkusen, Fed. Rep. of Germany

[21] Appl. No.: 140,913

[22] Filed: Apr. 16, 1980

[30] Foreign Application Priority Data

May 4, 1979 [DE] Fed. Rep. of Germany ....... 2918023

[51] Int. Cl.$^3$ .............................................. C07C 85/06
[52] U.S. Cl. ................................... 564/305; 564/428; 564/431; 564/440; 564/442; 564/443
[58] Field of Search ................ 260/571, 574, 576, 577

[56] References Cited

U.S. PATENT DOCUMENTS

| 3,914,274 | 10/1975 | Begland | 260/465.5 R |
| 4,067,903 | 1/1978 | Hoch et al. | 260/570.6 |
| 4,185,035 | 1/1980 | Eizember et al. | 260/577 |

FOREIGN PATENT DOCUMENTS

| 2113978 | 10/1972 | Fed. Rep. of Germany | 260/571 |
| 2640618 | 3/1977 | Fed. Rep. of Germany | 260/576 |

OTHER PUBLICATIONS

Ogata et al., "Polym. J.", vol. 7(3), pp. 412–414 (1975).
Harris et al., "Aust. J. Chem.", vol. 30(10), pp. 2213–2223 (1977).
Dzharov, "Farmatsiya (Sofia)", (Med. Akad. Sofia, Bulg.), vol. 27(6), pp. 1–5 (1977).

*Primary Examiner*—John Doll
*Attorney, Agent, or Firm*—Sprung, Felfe, Horn, Lynch & Kramer

[57] ABSTRACT

In a process for the preparation of an N-alkylated aromatic amine by contacting an aromatic amine with an aliphatic or cycloaliphatic alcohol at an elevated temperature and under increased pressure, in the presence of catalysts, the improvement wherein the reaction is carried out in the presence of a phosphorus oxyhalide.

6 Claims, No Drawings

PROCESS FOR THE PREPARATION OF N-ALKYLATED AROMATIC AMINES

The invention relates to a process for the preparation of N-alkylated aromatic amines by reacting aromatic amines with aliphatic or cycloaliphatic alcohols in the presence of phosphorus oxyhalides.

The N-alkylation of aromatic amines with alcohols in the presence of reaction accelerators is known from Houben-Weyl, Methoden der organischen Chemie (Methods of Organic Chemistry), Volume XI/1, pages 134 to 143, Thieme, Stuttgart 1962. Inorganic acids, such as hydrogen halide acids, sulphuric acid and phosphoric acid, and metal salts, such as zinc chloride, iron-III chloride or copper-II chloride, are mentioned as reaction accelerators. In addition, iodine, boron trifluoride and phosphorus trichloride can also be used.

The disadvantage of using the particularly active catalysts, such as the hydrogen halide acids, phosphorus trichloride or elementary iodine, is their highly corrosive effect on the equipment and pipelines made of iron or iron alloys.

A process has been found for the preparation of N-alkylated aromatic amines by reacting aromatic amines with aliphatic or cycloaliphatic alcohols at elevated temperature and under increased pressure, in the presence of catalysts, which is characterised in that the reaction is carried out in the presence of phosphorus oxyhalides.

Examples which may be mentioned of phosphorus oxyhalides which can be employed in the process according to the invention are: phosphorus oxychloride and phosphorus oxybromide. Phosphorus oxychloride is preferably employed.

The phosphorus oxyhalides can be employed in the process according to the invention individually or as mixtures with one another.

The phosphorus oxyhalides are in general employed in the process according to the invention in an amount of about 0.05 to about 2.0% by weight, preferably in an amount of about 0.1 to about 1.0% by weight, relative to aromatic amine employed and to aliphatic or cycloaliphatic alcohol employed.

Aromatic amines which can be employed in the process according to the invention are those of the general formula I

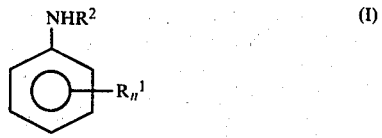

in which
R$^1$ represents halogen or a lower alkyl, alkoxy or alkylmercapto radical,
R$^2$ represents hydrogen or a lower alkyl radical and
n denotes one of the numbers 0, 1, 2 or 3, it also being possible for the radicals R$^1$ to differ in the case where n represents 2 or 3.

Further aromatic amines which can be employed in the process according to the invention are those of the general formula II

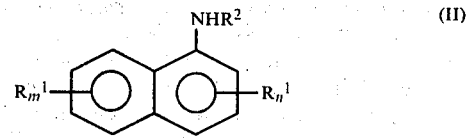

in which
R$^1$ and R$^2$ have the meaning indicated in formula (I) and
n and m independently of one another have the meaning indicated for n in formula (I).

Halogens which may be mentioned are fluorine, chlorine, bromine and iodine, preferably chlorine and bromine.

Lower alkyl radicals which may be mentioned are those with up to 4 C atoms, preferably up to 2 C atoms; examples are the methyl, ethyl, propyl and butyl radical, preferably the methyl and ethyl radical.

Possible alkoxy radicals are those with up to 4 C atoms, preferably with up to 2 C atoms; examples which may be mentioned are the methoxy, ethoxy, propoxy and butoxy radical, preferably the methoxy and ethoxy radical.

Alkylmercapto radicals which may be mentioned are those with up to 4 C atoms, preferably with up to 2 C atoms; examples are the methylmercapto, ethylmercapto, propylmercapto and butylmercapto radical, preferably the methylmercapto and ethylmercapto radical.

Those aromatic amines of the formula (I) and (II) in which
R$^1$ represents chlorine, methyl or ethyl,
R$^2$ represents hydrogen, methyl or ethyl and
n and m are 0, 1 or 2, in particular 0 or 1, are particularly preferably employed as the starting material in the process according to the invention.

Examples which may be mentioned as representatives of the aromatic amines of the formula (I) and (II) which can be alkylated by the process according to the invention are: aniline, 1-naphthylamine, o-, m- and p-toluidine, o-, m- and p-ethylaniline, the xylidines, such as 2,3-, 2,4-, 2,5-, 2,6-, 3,4- and 3,5-dimethylaniline, 4-methyl-1-naphthylamine, the chlorine-substituted anilines, such as 2-chloro-, 3-chloro- and 4-chloro-aniline, 3-chloro-o-, 4-chloro-o-, 5-chloro-o-, 4-chloro-m-, 6-chloro-m-, 2-chloro-p- and 3-chloro-p-toluidine and 4-chloro- and 5-chloro-1-naphthylamine.

In principle, all the aliphatic or cycloaliphatic alcohols can be employed in the process according to the invention if they fulfil the condition of adequate stability under the reaction conditions.

Aliphatic alcohols with 1 to 10 carbon atoms and cycloaliphatic alcohols with 4 to 10 carbon atoms are preferred, and those aliphatic alcohols with 1 to 6 carbon atoms and cycloaliphatic alcohols with 5 to 8 carbon atoms are particularly preferred.

Examples which may be mentioned are: methanol, ethanol, n-propanol, i-propanol, n-butanol, i-butanol, tert.-butanol, n-pentanol, i-pentanol, hexanol, heptanol, octanol, cyclo-butanol, -pentanol, -hexanol, -heptanol and -octanol, 2-methyl-, 3-methyl- and 4-methyl-cyclohexanol, 2-ethyl-cyclohexanol, 3,3,5-trimethylcyclohexanol, 4-tert.-butylcyclohexanol and menthol.

Particularly preferred alcohols which may be mentioned are: methanol, ethanol, n-propanol, i-propanol, n-butanol and cyclohexanol.

The molar ratio of aromatic amine to aliphatic or cycloaliphatic alcohols can vary within wide limits. In general, the molar ratio of aromatic amine to aliphatic or cycloaliphatic alcohol is in the range from about 1:0.5 to about 1:20, and is preferably 1:0.7 to 1:5.

The process according to the invention can be carried out at temperatures in the range from about 200° to 400° C., preferably at 230° to 320° C.

The pressures are in general about 30 to about 200 bar, preferably 80 to 150 bar.

The reaction time depends on the starting components, the catalyst concentration, the reaction conditions, such as pressure and temperature, and the desired degree of conversion.

The reaction times are in general in the range from about 1 to about 10 hours.

The phosphorus oxyhalides employed according to the invention have a high catalyst activity in the N-alkylation of aromatic amines with aliphatic or cycloaliphatic alcohols, and it is particularly surprising that, in contrast to the known catalysts, the phosphorus oxyhalides according to the invention are scarcely corrosive towards the equipment and pipelines, which are usually made of iron or iron alloys, under the reaction conditions.

Further, the phosphorus oxyhalides have the property of forming no solid constituents either in the mixture of the starting components or in the mixture in which the reaction has finished, and this factor is exceptionally important for carrying out the N-alkylation of aromatic amines continuously.

Finally, in contrast to phosphorus trichloride, phosphorus oxychloride has a significant advantage with respect to working safety, since the phosphorus oxychloride in the alkylation mixture (aromatic amine plus alcohol) does not ignite spontaneously on contact with water.

The examples given below serve to illustrate the process according to the invention, but without restricting it to the examples.

EXAMPLE 1

A mixture of 1,860 g of aniline, 512 g of methanol and 3.1 g of $POCl_3$ is introduced into a 3 l autoclave with an up-and-down stirrer. After closing the autoclave, it is heated up to 280° C. and kept at this temperature for about 3 hours. A pressure of about 80 bar is thereby established. A crude oil is obtained which, according to the gas chromatogram, has the following composition (methanol is not taken into consideration): 39% of aniline, 43% of N-methylaniline and 17% of N,N-dimethylaniline.

After neutralizing with dilute sodium hydroxide solution, distilling off unreacted methanol and separating off the aqueous layer, the crude product was subjected to fractional distillation over a 150 cm packed column with a mirrored vacuum jacket, at a reflux ratio of about 20. 850 g of main runnings which, according to analysis by gas chromatography, consisted of 98.8% of N-methylaniline, 1.1% of N,N-dimethylaniline and traces of aniline, were taken off.

EXAMPLE 2

The batch from Example 1 is repeated with 6 g of $POBr_3$. The crude oil composition is: 35% of aniline, 46% of N-methylaniline and 18% of N,N-dimethylaniline.

EXAMPLE 3

A mixture of 749 g of p-toluidine, 1,008 g of methanol and 7.9 g of $POCl_3$ is introduced into a 3 l autoclave with an up-and-down stirrer. After closing the autoclave, it is heated up to 280° C. and kept at this temperature for about 3 hours. A pressure of about 60 bar is thereby established. A crude oil composed of <1% of p-toluidine, 1% of N-methyl-p-toluidine and 94% of N,N-dimethyl-p-toluidine is obtained.

EXAMPLE 4

A mixture of 1,116 g of aniline, 607 g of ethanol and 4.2 g of $POCl_3$ is employed in the same procedure as in Example 3. The crude oil composition is: 31% of aniline, 61% of N-ethylaniline and 8% of N,N-diethylaniline.

EXAMPLE 5

A mixture of 1,284 g of o-toluidine, 607 g of ethanol and 6.3 g of $POCl_3$ is employed in the same procedure as in Example 3. The crude oil composition is: 33% of o-toluidine, 63% of N-ethyl-o-toluidine and 3% of N,N-diethyl-o-toluidine.

EXAMPLE 6

A mixture of 1,285 g of m-toluidine, 720 g of i-propanol and 6.7 g of $POCl_3$ is employed in the same procedure as in Example 3. The crude oil composition is: 53% of m-toluidine, 45% of N-isopropyl-m-toluidine and 1 to 2% of N,N-diisopropyl-m-toluidine.

EXAMPLE 7

A mixture of 1,023 g of aniline, 814 g of n-butanol and 3.7 g of $POCl_3$ is employed in the same procedure as in Example 3. The crude oil composition is: 43% of aniline, 53% of N-n-butylaniline and 3% of N,N-di-n-butylaniline.

EXAMPLE 8

A mixture of 931 g of aniline, 1,002 g of cyclohexanol and 3.8 g of $POCl_3$ is employed in the same procedure as in Example 3. Crude oil composition: 73% of aniline, 22% of N-cyclohexylaniline and 1–2% of N,N-dicyclohexylaniline. Significant cyclohexanol losses occur through formation of cyclohexene.

EXAMPLE 9

A mixture of 931 g of 1-naphthylamine, 897 g of ethanol and 8.2 g of $POCl_3$ is employed in the same procedure as in Example 3. Crude oil composition: 30% of 1-naphthylamine, 52% of N-ethyl-1-naphthylamine and 6% of N,N-diethyl-1-naphthylamine.

EXAMPLE 10

Corrosion samples of the high-grade steels, namely material 1.4571 and 1.4439, were introduced into a unit for continuously alkylating aniline with methanol under high pressure to give N-methyl-aniline and N,N-dimethyl-aniline. The reaction conditions were kept constant and, specifically, were as follows: molar ratio of aniline:methanol=1:1; 0.117% of $POCl_3$, relative to the alkylation mixture. Reaction temperature: 270° C.; pressure: 100 bar.

After an operating time of 36 days, the wear due to corrosion was determined:
material 1.4571: 0.235 mm/year
material 1.4439: 0.307 mm/year.

COMPARISON EXAMPLE

The corrosion test according to Example 10 was repeated under identical conditions, but using 0.1% of $PCl_3$, relative to the alkylation mixture.

After an operating time of 35 days, the wear due to corrosion was again determined:

material 1.4571: 1.144 mm/year
material 1.4439: 2.096 mm/year.

What is claimed is:

1. In a process for the preparation of an N-alkylated aromatic amine by contacting an aromatic amine with an aliphatic or cycloaliphatic alcohol at an elevated temperature and under increased pressure, in the presence of catalysts, the improvement wherein the reaction is carried out in the presence of a phosphorus oxyhalide.

2. A process according to claim 1 wherein phosphorus oxychloride and/or phosphorus oxybromide is employed as the phosphorus oxyhalides.

3. A process according to claim 1 wherein the phosphorus oxychloride is employed as the phosphorus oxyhalide.

4. A process according to claim 1 wherein the phosphorus oxyhalide is employed in an amount of 0.05 to 2.0 percent by weight, relative to aromatic amine employed and to aliphatic or cycloaliphatic alcohol employed.

5. A process according to claim 1 wherein said aromatic amine has the formula

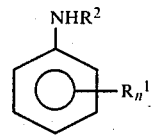

in which
- $R^1$ represents halogen or a lower alkyl, alkoxy or alkylmercapto radical,
- $R^2$ represents hydrogen or a lower alkyl radical and
- n denotes one of the numbers 0, 1, 2, or 3, it also being possible for the radicals $R^1$ to differ in the case where n represents 2 or 3.

6. A process according to claim 1 wherein said aromatic amine has the formula

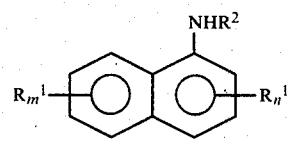

in which
- $R^1$ represents halogen or a lower alkyl, alkoxy or alkylmercapto radical,
- $R^2$ represents hydrogen or a lower alkyl radical and
- n and m independently of one another denote one of the numbers 0, 1, 2, or 3, it also being possible for the radicals $R^1$ to differ in the case where n and/or m represent 2 or 3.

* * * * *